(12) United States Patent
Kuzma et al.

(10) Patent No.: US 8,019,439 B2
(45) Date of Patent: Sep. 13, 2011

(54) LEAD ASSEMBLY AND METHOD OF MAKING SAME

(75) Inventors: Janusz A Kuzma, Bayview (AU); Anne M Pianca, Santa Monica, CA (US); Jeryle L Walter, Valencia, CA (US); Milad Girgis, North Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1035 days.

(21) Appl. No.: 11/689,918

(22) Filed: Mar. 22, 2007

(65) Prior Publication Data

US 2007/0168007 A1 Jul. 19, 2007

Related U.S. Application Data

(63) Continuation-in-part of application No. 11/329,907, filed on Jan. 11, 2006, now Pat. No. 7,891,085.

(60) Provisional application No. 60/643,093, filed on Jan. 11, 2005.

(51) Int. Cl.
*A61N 1/05* (2006.01)
(52) U.S. Cl. .......................... 607/116; 607/117; 607/119
(58) Field of Classification Search ................ 607/116, 607/122, 115, 117, 118, 119, 120, 121; 600/373
See application file for complete search history.

(56) References Cited

U.S. PATENT DOCUMENTS

| | | | |
|---|---|---|---|
| 3,769,984 A | 11/1973 | Muench | |
| 4,379,462 A * | 4/1983 | Borkan et al. | 607/117 |
| 4,953,564 A * | 9/1990 | Berthelsen | 607/120 |
| 5,555,618 A | 9/1996 | Winkler | |
| 6,055,456 A | 4/2000 | Gerber | |
| 6,205,361 B1 | 3/2001 | Kuzma et al. | |
| 6,216,045 B1 * | 4/2001 | Black et al. | 607/122 |
| 6,249,708 B1 | 6/2001 | Nelson et al. | |
| 6,551,302 B1 | 4/2003 | Rosinko et al. | |
| 6,847,849 B2 * | 1/2005 | Mamo et al. | 607/117 |
| 2005/0215945 A1 | 9/2005 | Harris et al. | |

* cited by examiner

*Primary Examiner* — Carl H Layno
*Assistant Examiner* — Pamela M Bays
(74) *Attorney, Agent, or Firm* — Frommer Lawrence & Haug LLP; Patrick R. Turner (57) ABSTRACT

A lead assembly and a method of making a lead are provided. The lead comprises a terminal, proximal end having a plurality of terminal contacts and material separating the terminal contacts. In one embodiment of the lead, the terminal contacts are separated by a preformed spacer, that may be made from various hard materials such as polyurethane, PEEK and polysulfone. Epoxy may be used to fill spaces at the proximal lead end, including between the spacer and terminal contacts. In one embodiment of the lead, the terminal contacts are separated by epoxy only. The lead may include a plurality of conductor lumens that contain conductors. The lead may also include a stylet lumen for accepting a stylet.

28 Claims, 8 Drawing Sheets

LEAD ASSEMBLY AND METHOD OF MAKING SAME

This application is a continuation-in-part of U.S. patent application Ser. No. 11/329,907, filed Jan. 11, 2006, now U.S. Pat. No. 7,891,085, which claims the benefit of provisional application Ser. No. 60/643,093, filed Jan. 11, 2005. Both the '907 and '093 applications are herein incorporated by reference in their entireties.

FIELD OF THE INVENTION

The present invention relates to implantable leads for providing electrical stimulation.

BACKGROUND

Many types of implantable leads are currently used to treat a variety of maladies. In one example, a multiple electrode contact lead is used to treat chronic pain through stimulation of the spinal cord. "Electrode contact" will be used herein to refer to that conductive surface on the lead that delivers or sinks electrical current to or from tissue. Typical electrode contact material are platinum or platinum/iridium alloy.

Spinal cord stimulation systems generally have two implantable components: an implantable pulse generator (IPG) and at least one stimulation lead connected to one output of the IPG. Generally, however, the IPG is a multi-channel device capable of delivering electrical current through the multiple electrode contacts of the lead.

The term "lead" used herein will refer generally to any elongate device having any conductor or conductors, covered with an insulated sheath and having at least one terminal (connector) contact attached to the elongate device, usually at the proximal portion of the elongate device. As broadly used, the term "lead" may refer to a "stimulation lead" such as a percutaneous or linear lead, a paddle type lead, an extension lead or an adapter lead, which is a type of extension lead. A stimulation lead may have a stylet lumen running through most of the length of the lead and which lumen has an opening at the proximal end of the lead. A stylet, which is a thin wire or wire-like implement made from metal or some other stiff and resilient material, e.g., ceramic or plastic, may be placed into the stylet lumen during steering and implantation of the lead. The stylet, inserted into the lumen, can help stiffen the lead so that the stylet/lead combination may be more easily inserted through tissue. After the lead is positioned at a desired location in the body, the stylet is withdrawn from the stylet lumen and then the stylet is typically discarded.

There are two types of stimulation leads that may be used with the IPG. The first type of stimulation lead is a paddle lead, which has a multiplicity of electrode contacts spread out over a flat, paddle-like surface that is attached to one end of the lead. A paddle lead advantageously permits the electrode contacts to be spaced apart to provide wide coverage over a stimulation area. A disadvantage presented with a paddle lead is that it usually requires a laminectomy or laminotomy, which are highly invasive surgical procedures necessary to implant the large, non-isodiametric paddle.

A second type of stimulation lead is commonly used is a "percutaneous" or "linear" lead, having multiple electrode contacts positioned along the distal portion of the lead. U.S. Pat. No. 6,205,361 issued to Baudino et al., for example, describes the making of a multi-contact electrode array for a lead. The distal end of the lead may be about the same thickness or diameter as the remainder of the lead. Such a lead is sometimes also referred to as an "isodiametric" lead because the lead may have the same thickness or, in the case of a lead have a circular cross-section, the same diameter, along the length of the lead. The percutaneous (linear) lead is dimensionally configured for tunneling to a target stimulation site. No invasive surgical procedure such as a laminotomy is required; the percutaneous lead may be placed through an epidural type large-bore needle reducing surgical trauma.

Whether the lead is a stimulation lead such as a paddle type or a percutaneous lead or whether the lead is an extension lead or an adapter type lead, it is sometimes desired to control the stiffness and flexibility of the proximal (terminal or connector) portion of the lead relative to the remainder of the lead.

It would be desirable to have designs and methods for making the proximal (terminal) connector portion of a lead having multiple terminal contacts, which designs and methods yield a connector portion with a desired stiffness, flexibility and buckling resistance.

BRIEF SUMMARY

Embodiments of lead designs, with specific proximal connector ends, and methods of manufacturing these lead designs are provided. The proximal end of the lead has at least two terminal contacts for connecting to a connector block of an IPG, which connector block accepts insertion of the proximal (connector) end of the lead. The distal portion of the lead can be any configuration including a linear or percutaneous design or a paddle type design or the female connector or receptacle of an extension lead or an adapter lead.

The proximal portion of every lead always has a connector end with a plurality of terminal contacts as part of the connector. As an example, the connector may have eight terminal contacts. In one embodiment, a terminal spacer is placed between adjacent terminal contacts. Small spaces and voids between the terminal spacer and terminal contacts are filled up using an implantable grade epoxy which is allowed to harden during manufacture of the lead. The terminal spacers can be chosen from a number of implantable materials to yield a desired mechanical characteristic for the proximal (terminal or connector) end of the lead. The terminal spacers may be chosen from among the following implantable materials: polyurethane, polyetherether ketone or polyarylether ketone (both types of ketones, collectively referred to hereinafter as "PEEK"), polysulfone, polyester, polyethylene or silicone. The terminal spacers can be ring shaped or ring-like in configuration and can be pre-formed. The terminal contacts can also be ring shaped or ring-like in configuration.

In another embodiment, the proximal portion of the lead has a plurality of terminal contacts. Thus the lead may have two, three or more terminal contacts. No terminal spacers are used at the proximal end of the lead. The terminal contacts are spaced apart by a specified distance. Epoxy is placed between two terminal contacts and allowed to harden.

The proximal end of the lead has multiple terminal contacts defining a connector having material between the terminal contacts. The material between the terminal contacts therefore may be a combination of terminal spacer material plus epoxy or solely epoxy. Often, the lead body insulation is a softer polyurethane or silicone material than the material between the terminal contacts. The use of epoxy alone or in combination with a chosen terminal spacer material can be used to yield a desired flexibility and buckling resistance at the proximal, connector end of the lead. Such buckling resistance may be desired or necessary with certain connector systems that require a specific insertion force. For example, spring-like connectors may be used in the IPG header. Spring-like connectors require a certain insertion force to engage the connector end of a lead. If the connector end is too soft or flexible, the medical practitioner can have a difficult time inserting the connector end of the lead into the connector block of the IPG without the lead buckling.

The distal end of the lead can be any configuration. In particular the distal end of the lead may be linear or paddle shaped to provide a stimulation lead. If the lead has a linear distal end, the electrode contacts can be spaced apart from each other by placing electrode contact spacers between adjacent electrode contacts. The electrode contact spacers may be made of polyurethane or, conceivably, some other spacer materials including PEEK, polyester, polyethylene, polysulfone or silicone. Generally, however, it is desirable to keep the distal end of the lead relatively pliable and, hence, a flexible electrically insulative material such as polyurethane or silicone is preferred at the distal end. The electrode spacers may be ring shaped or ring-like in configuration. The electrode contacts may also be rings or ring-like in configuration.

If the distal end of the lead is a paddle, the paddle must generally have at least one major flat surface. Electrode contacts may be placed in various arrangements over the flat surface. The paddle itself may be made from a relatively flexible material such as polyurethane or silicone to allow the paddle to conform to tissue.

The lead may also be an extension lead having the usual proximal multiple, terminal contacts at the connector end but also having a distal end with a female connector or receptacle for accepting the proximal, connector end of a stimulation lead such as a percutaneous lead or a paddle lead as described.

The lead, whether a linear, paddle, extension or adapter lead, may optionally include a preformed lead body. The lead body is the middle portion of a lead and can be made from a relatively flexible insulative material such as silicone or polyurethane. Such a lead body may have individual conductor lumens that carry individual conductors within each conductor lumen. Each conductor may be constructed of multiple strands of smaller conductor wires. The lead body may also include a larger, stylet lumen running the length of the lead body. The stylet lumen may be configured and sized to accept the insertion of a stylet or guide to help implant and guide the lead during implantation. The stylet lumen may be centrally or axially located while the conductor lumens are placed peripherally around the axially positioned stylet lumen. The lead body, made of polyurethane or silicone, and having conductor lumens and/or a stylet lumen can be extruded using known extrusion methods.

Also discussed herein are methods of making the various embodiments of the proximal, connector portions of leads and of the leads themselves. In particular the methods are for making a lead having a connector end with terminal contacts, terminal spacers and epoxy and for a connector with terminal contacts and only epoxy without spacers. The methods of making leads includes embodiments for making linear, paddle, extension and adapter leads with the particular connector ends described.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figures 1, 2:
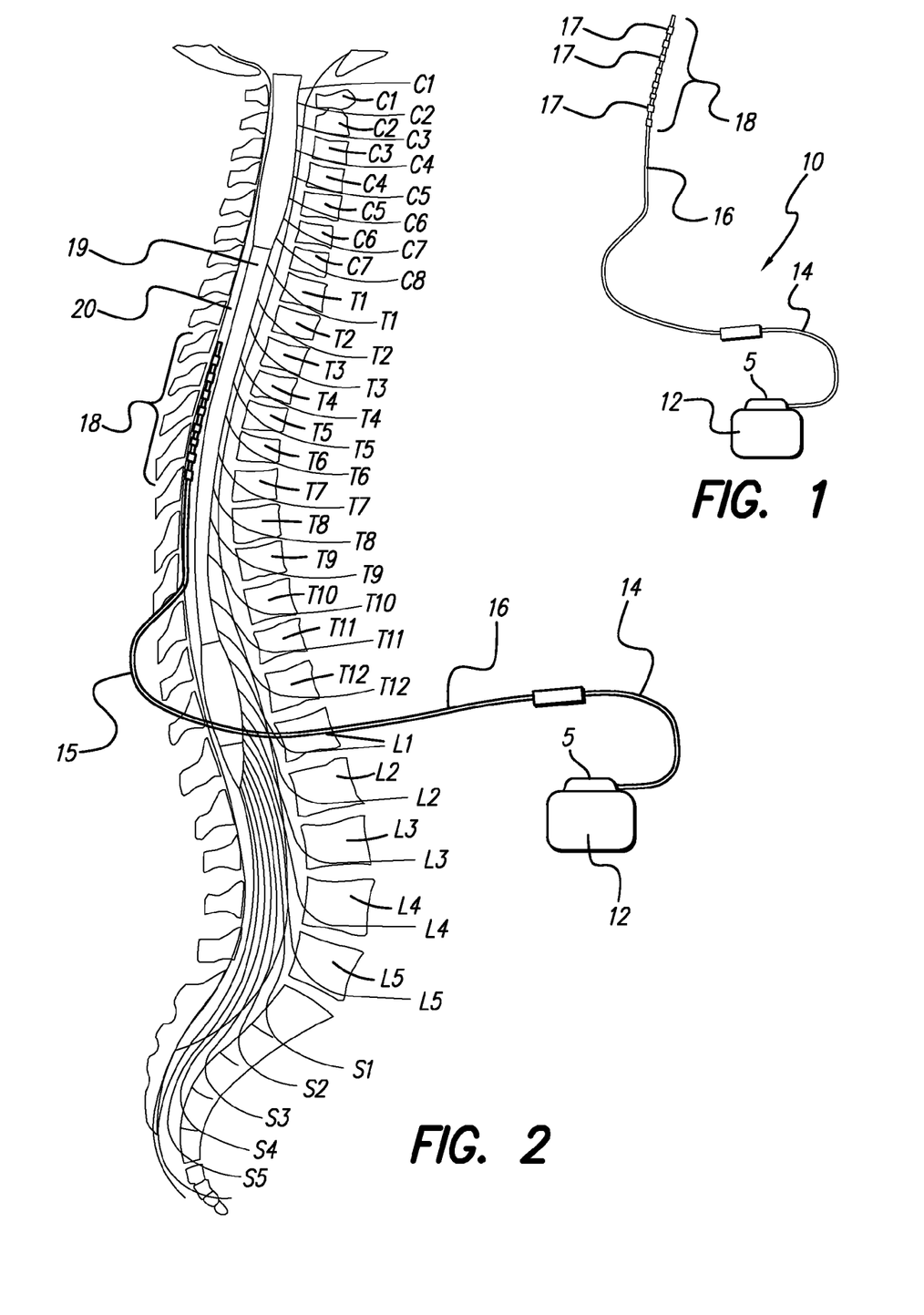
FIG. 1 shows a generalized spinal cord stimulation system with a exemplary percutaneous lead connected to an implantable pulse generator ("IPG")
FIG. 2 shows an illustration of the percutaneous lead implanted into the epidural space of a human spinal cord.

FIG. 1 shows a generalized stimulation system that may be used in spinal cord stimulation (SCS), as well as other stimulation applications. Such a system typically comprises an implantable pulse generator ("IPG") 12, an optional lead extension 14, a linear or percutaneous stimulation lead 16 and an electrode array 18 that is part of the linear stimulation lead. The electrode array 18 includes a plurality of electrode contacts 17. In a percutaneous lead, the electrode contacts 17 can be arranged in an in-line electrode array 18 at the distal end of the lead 16. Other electrode array configurations can also be used. The IPG 12 generates stimulation current pulses that are applied to selected electrode contacts 17 within the electrode array 18.

The proximal end of the extension lead 14 (sometimes also referred to alternatively as a "lead extension") can be removably connected to the IPG 12 and a distal end of the extension lead 14 can be removably connected to a proximal end of the lead 16. The electrode array 18 is formed on a distal end of the percutaneous stimulation lead 16. The in-series combination of the extension lead 14 and percutaneous lead 16 conduct the stimulation current from the IPG 12 to electrode contacts 17 of the electrode array 18. It is noted that the extension lead 14 need not always be used with the neural stimulation system 10. Instead, the extension lead 14 may optionally be used when the physical distance between the IPG 12 and the electrode array 18 requires its use or, sometimes, for the purpose of a temporary trial procedure. The IPG 12 includes a header piece or connector block 5 which has at least one opening to accept the connector end of an extension lead 14 or the proximal, connector end of lead 16. In some cases, the connector block 5 can have two openings to accept the connector ends of two stimulation leads or extension leads.

The IPG 12 contains electrical circuitry and can be powered by an internal primary (one-time-use-only) or a rechargeable battery, which through the use of electrical circuitry can output current pulses to each stimulation channel. Communication with the implanted IPG can be accomplished using an external programmer (not shown), typically through a radio-frequency (RF) link.

FIG. 2 shows a transverse, mid-sagittal view of a spinal cord and a generalized, implantable, spinal cord stimulation system. The stimulation system shown is being used as a spinal cord stimulator (SCS) system. In such an application, the percutaneous stimulation lead 16 and, more particularly, the electrode array 18 are implanted in the epidural space 20 of a patient in close proximity to the spinal cord 19. Because of the lack of space near the lead exit point 15 where the electrode lead 16 exits the spinal column, the IPG 12 may be implanted in the abdomen or above the buttocks. Use of an extension lead 14 facilitates locating the IPG 12 away from the lead exit point 15.

Figure 3A:
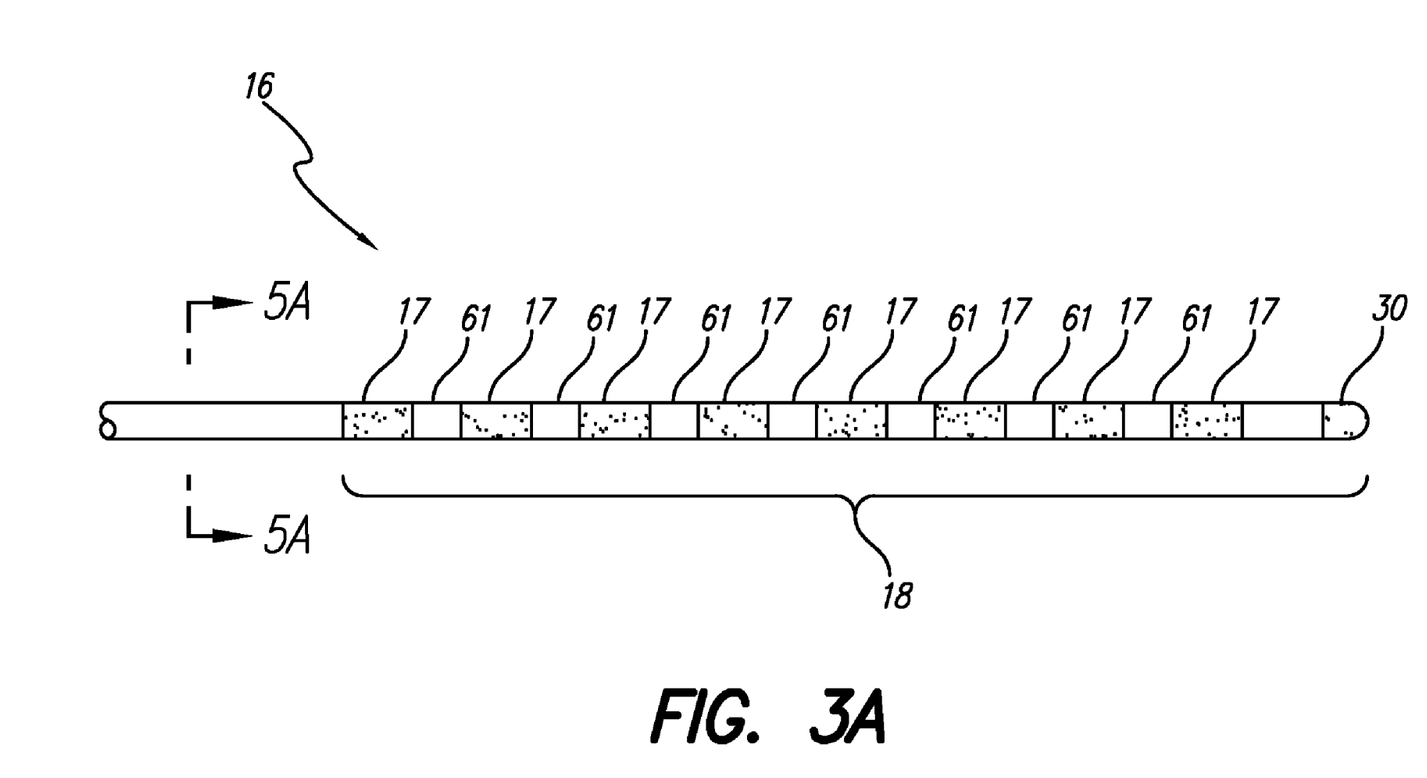
FIG. 3A shows a side view of the distal end of a percutaneous lead.

FIG. 3A shows the distal end of a linear or percutaneous lead 16, showing electrode contacts 17 and insulative material 61 between electrode contacts, defining the electrode array 18.

Figure 3B:
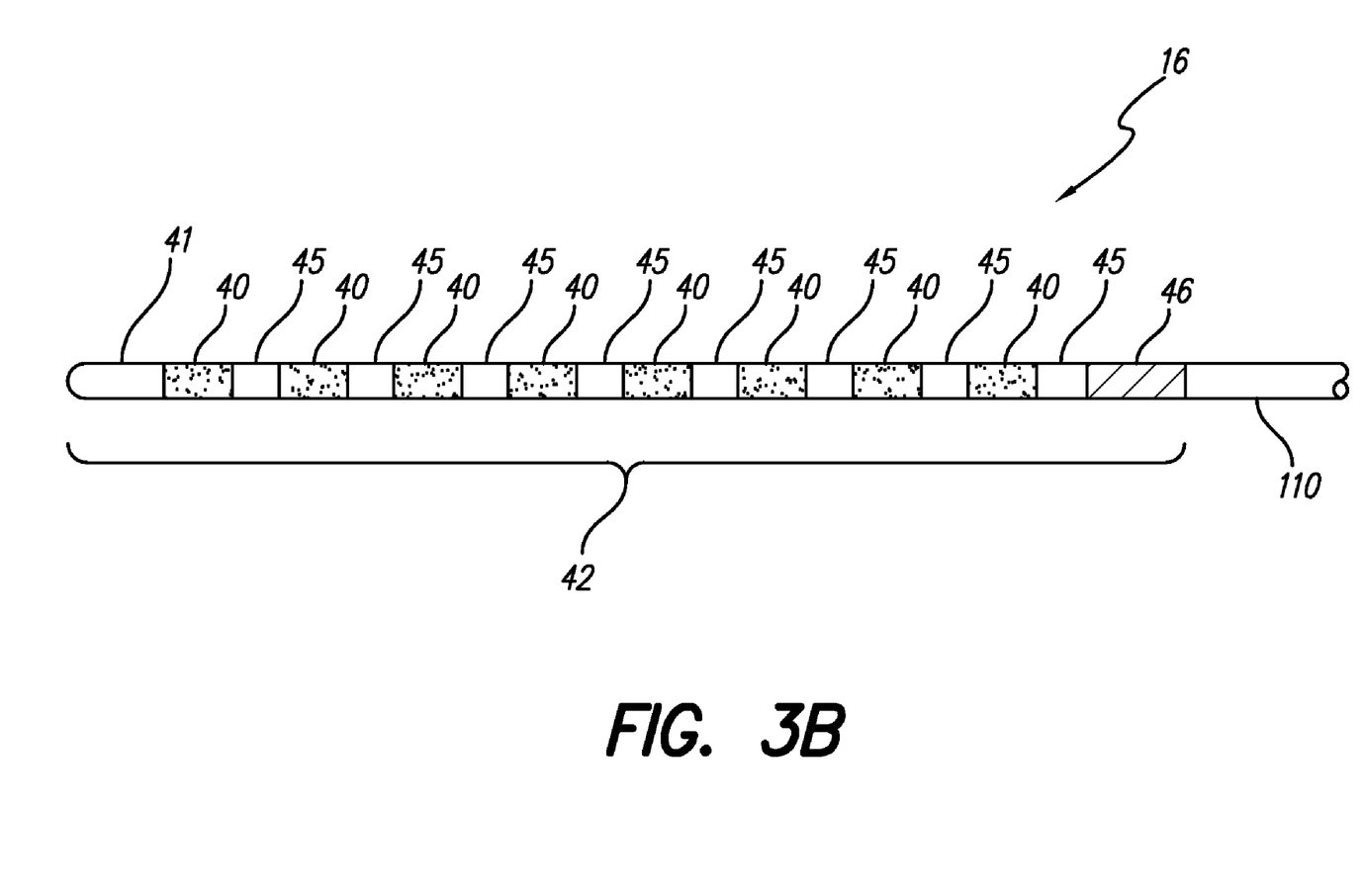
FIG. 3B shows a side view of the proximal (connector) end of the percutaneous lead shown in FIG. 3A.

FIG. 3B shows a depiction of the proximal end of the percutaneous stimulation lead 16. This proximal lead end, may include eight, electrically conductive, terminal (or connector) contacts 40, and may also include a contact tip element 41. Collectively, the lead end, including the connector (terminal) contacts 40, will be called herein as the proximal, lead connector end 42 of the stimulating lead 16. Terminal (or connector) contact spacers 45 are placed between the terminal contacts 40. Typically the spacers 45 are an electrically insulative material.

Figure 4:
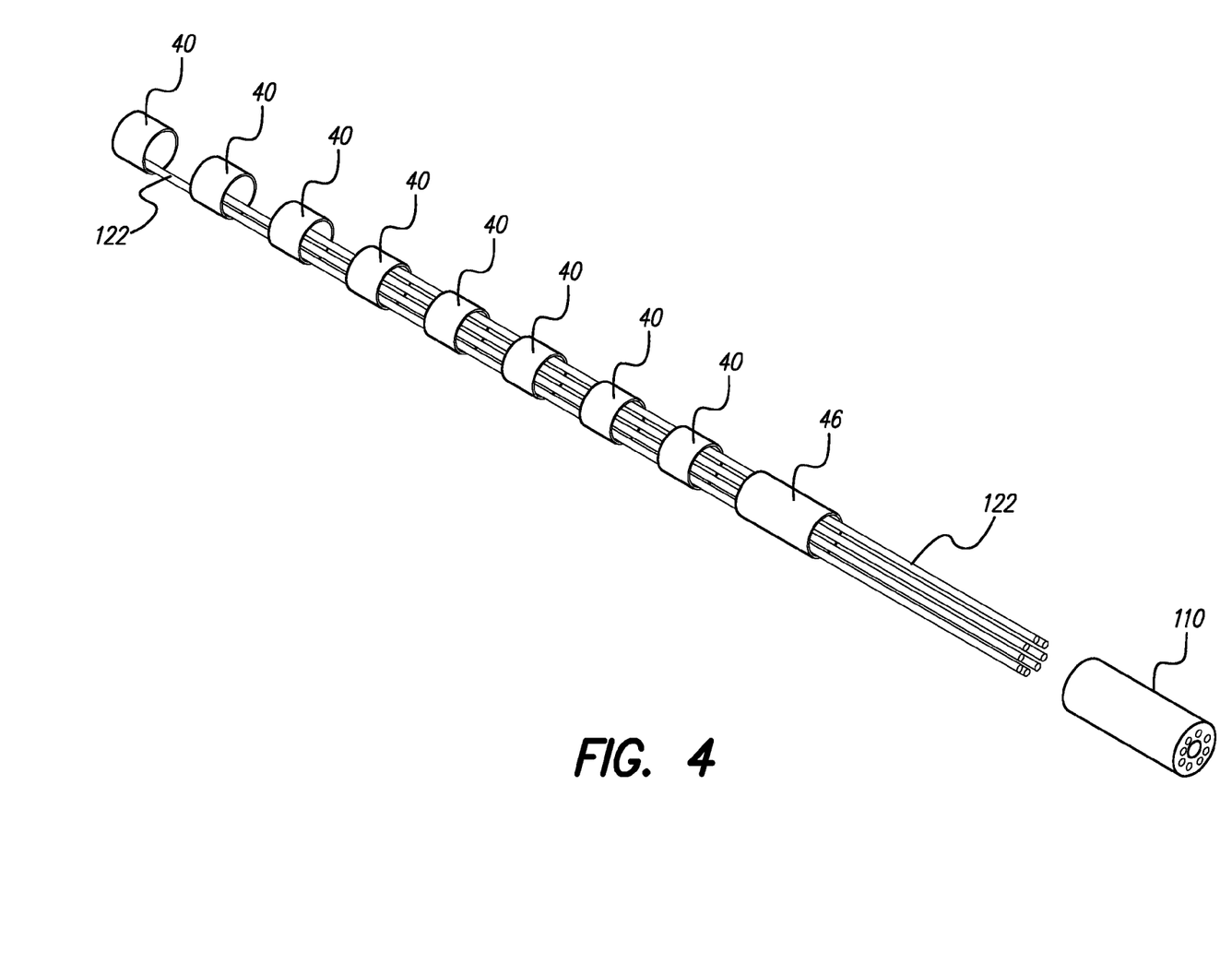
FIG. 4 shows a view of the proximal, terminal end of the lead assembly showing the terminal (connector) contacts and conductor wires that connect to each terminal (connector) contact.

Referring to FIGS. 3B and 4, the terminal contacts 40 may be made from a non-corrosive, electrically conductive material, e.g., platinum/iridium alloy or platinum. Contact tip 41, however, is not electrically connected to any conductor and contact tip 41 may merely serve as a hard surface for a mechanical contact securing device, such as a set screw (not shown), which may be used to secure the lead connector end 42 with the connector block of the IPG 12. Contact tip 41 is optional and does not need to be included as part of the lead. Instead, the contact tip of the lead may be of similar or the same insulation material as the remainder of the lead 16 or lead body 110 (FIG. 5C). Cylindrical ring element ("retention sleeve") 46 is also optional and not connected to any conductor. The retention sleeve 46, which may be made of non-corrosive metal such as titanium, stainless steel or platinum/iridium alloy, may also be used to secure a set screw (not shown) that is located in the connector block 5 (shown in FIG. 2). When the set screw is screwed into the connector block 5, the end of the screw contacts the retention sleeve 46 and mechanically secures the proximal, connector end of the lead within the connector block 5 and prevents the connector end of the lead from being removed.

FIG. 4 shows a proximal lead assembly with each of the terminal (connector) contacts 40 welded to a respective one of a plurality of conductors 122. A portion of the lead body 110 is shown. The conductors 122 are inserted into individual conductor lumens in the lead body 110. Each of the eight terminal contacts 40, as shown, are connected to a conductor 122 which, in turn, are connected to a respective electrode contact 17 at the distal end of the stimulating lead 16. The connection may be a weld. The insulating material between the terminal contacts 40 and around the conductors 122 is not shown in FIG. 4 for purposes of better illustrating the connection between each conductor and its respective terminal contact. Cylindrical ring element ("retention sleeve") 46 is optional and is not connected to any conductor. The retention sleeve 46 may be used as a contact element for a mechanical securing device such as a set screw in order to secure the percutaneous stimulation lead 16 to the IPG 12. Alternatively or, in addition, the retention sleeve 46 may function as a radiopaque element, provided that the material used for element 46 is radiopaque.

The shape of the terminal spacers 45 (FIG. 3B) can be a ring, ring-like or a short, cylindrical tube. One efficient way of manufacturing the terminal spacers 45 is to extrude or form a long tube and then cut short segments of the tube to create each terminal spacer 45. Other known methods may be used to make each terminal spacer 45. The terminal spacer 45 is therefore pre-formed before being assembled with other components of the stimulation lead 16.

The terminal spacers 45 may be made from an implantable grade polyurethane such as Pellethane® 55D thermoplastic material. Alternatively, the terminal spacers 45 may be made from polyarylether ketone or polyetherether ketone. As used herein, we will refer, collectively, to both types of ketones as "PEEK" material. In another embodiment, the terminal spacers 45 may be made from polysulfone. In yet other embodiments, the terminal spacers may be made from polyester, polyethylene or silicone.

An epoxy material may be applied between any void space within the terminal spacers 45 and terminal contacts and small voids between the terminal spacer 45 and terminal contacts 40 and, sometimes, within at least some portion of the conductor lumens (when a preformed lead body with conductor lumens is used) near the proximal end of the lead. The epoxy material should be implantable grade. In one embodiment, where the proximal end of the lead is intended to be stiffer than the middle portion of the lead, the epoxy may be an 85D (durometer hardness) material although other hardness grades of epoxy may be used to achieve a desired stiffness at the proximal end of the lead. The epoxy material may be deliberately chosen to create a proximal end of the lead which is stiff and relatively inflexible compared to the middle portion of the lead. The extra stiffness at the proximal end of the lead may be desirable in order to facilitate insertion of the proximal end of the lead into a connector header 5 that is attached to an IPG 12.

In yet another embodiment, the material separating the terminal contacts on the proximal end of the lead may not use preformed terminal spacers 45 between the terminal contacts. Instead, only epoxy is placed between the terminal contacts. Once cured, the epoxy may be a relatively hard and inflexible material compared to the other parts of the lead that employs insulation which may be made of a softer polyurethane or silicone. An epoxy that is 85D hardness material can be used to provide a stiffer connector end compared to a lead body that is made from a 55D polyurethane.

Figure 5A:
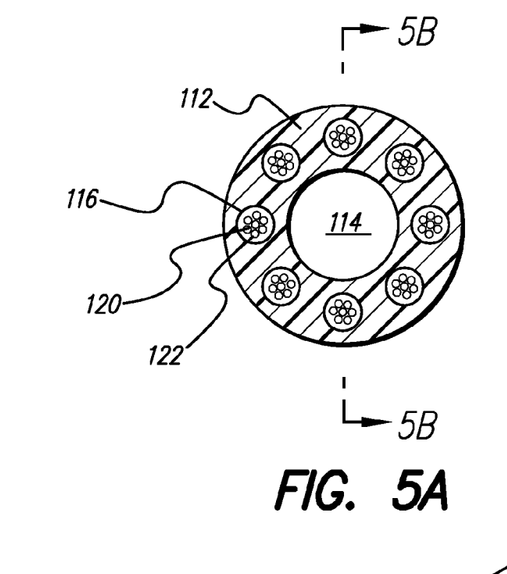
FIG. 5A shows a cross-sectional view of the percutaneous lead shown in FIG. 3A at line 5A-5A.

FIG. 5A shows a cross-sectional view of a lead body, for example, of FIG. 3A along line 5A-5A.

Figure 5B:
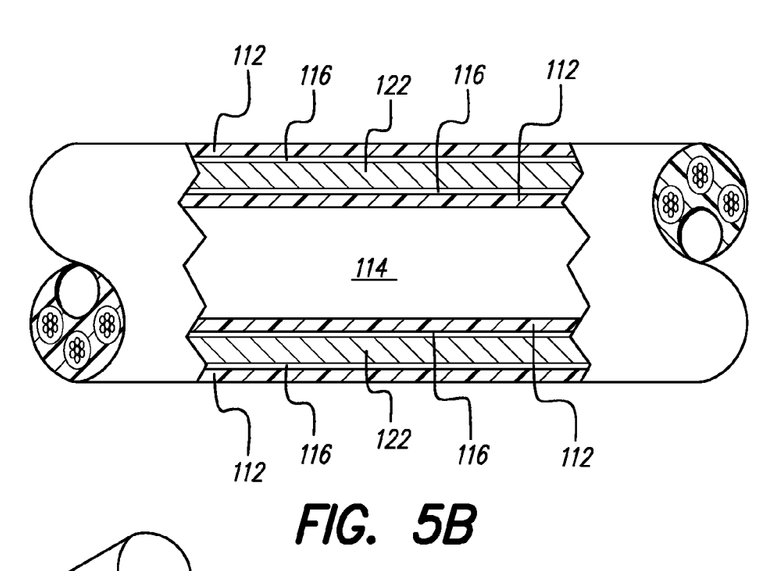
FIG. 5B shows a cross-sectional view of the percutaneous lead shown in FIG. 5A along line 5B-5B.
Figure 5C:
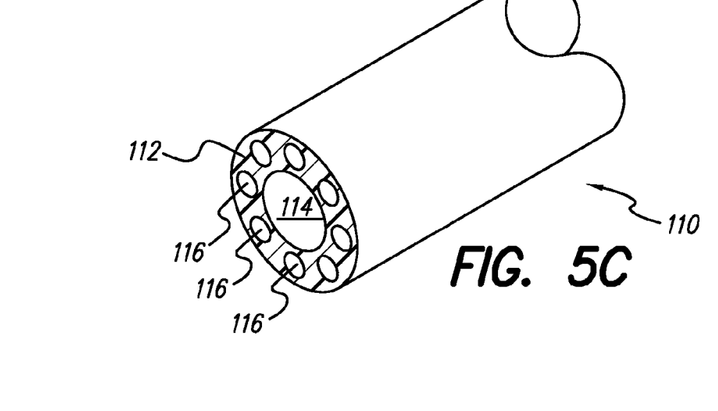
FIG. 5C shows a perspective view of an embodiment of the lead body, having an axially positioned stylet lumen and peripherally surrounding smaller conductor lumens for containing conductor wires.

FIG. 5B shows a partial, longitudinal, cross-sectional view of the lead body along the line 5B-5B.

FIG. 5C shows a perspective view of an exemplary lead body 110 of the lead 16, excluding conductor wires. The lead body 110 is that portion of the lead insulation 112 that is between the distal electrode contact array 18 and the array of terminal (connector) contacts 40 (FIG. 4) at the proximal lead end 42. The lead body 110 may be extruded as a one-piece component. Note the central stylet lumen 114 and the surrounding eight conductor lumens 116.

FIGS. 5A and 5B show an exemplary embodiment of an insulation section 112 of the lead body 110 having eight lumens 116 containing the conductor (wires) 122, having individual strands 120. For example, fifteen or sixteen individual conductor strands 120 may be braided or bundled into a single conductor 122. Also shown is a central lumen 114 that may be used to accept an insertion stylet (not shown) within the lumen to facilitate lead implantation. The opening of the lumen occurs at the proximal end of the lead 16. The lead body 110 may be a biocompatible, insulating lead material. Preferably the lead body 110 is made from a polyurethane. In particular the material may be Pellethane® thermoplastic material, e.g. 55D, 65D, or other durometer hardness. As previously indicated for FIG. 5C, the lead body 110 shown in FIG. 5B may be extruded as one piece. It should be understood that the lead body 110 is only one possible configuration that could be used and other types of lead bodies having different configuration could be used. For example, the lead body may not have a stylet lumen, but only a single conductor lumen that contains all the conductors. The construction of the lead body does not prevent the construction of a proximal end of the lead having multiple terminal contacts separated by insulative material or materials, e.g., spacers or epoxy.

The lead has at least two terminal contacts at the proximal, connector end of the lead. There are two embodiments of materials that can be placed between the terminal contacts: (1) the first embodiment uses terminal spacers, with epoxy or another adhesive-like, electrically insulative material filling the voids or spaces within the terminal spacers and terminal contacts and between a terminal spacer and a terminal contact or (2) epoxy alone filling the separation gap between adjacent terminal contacts.

The distal end of the lead can be any type of electrode configuration that is known. For example, the distal end of the lead may be linear or percutaneous or it may be a paddle shape. The following show in more detail leads having proximal or connector ends as described in (1) and (2) above.

FIG. 3A shows a distal portion of a linear or percutaneous lead 16 that may include embodiments of the proximal lead construction as described above. The stimulating lead 16 is used to stimulate neural tissue by delivering electrical stimulus pulses through at least one of the electrode contacts 17. The electrode contacts 17 can be separated by insulative material, for example, by electrode contact spacers ("electrode spacers") 61 that insulate the electrode contacts 17 from each other. A radiopaque marker 30 located at the distal tip of the lead 16 may be optionally included. Alternatively, the tip 30 of the lead may be the same material as the remainder of the lead insulation. The IPG 12 may be configured with a connector block 5 to permit connection to two stimulating leads, each having eight electrode contacts 17. A pair of stimulating leads 16 may be connected to an IPG 12 and an electrical circuit may be created between one electrode contact on the first lead and another electrode contact located on the second lead. The IPG 12, for example, may have sixteen independently programmable outputs that allow programming of pulse amplitude, pulse width and frequency of the pulse width. The electrode contacts 17 are to be made of a bio-compatible, electrically conductive electrode material such as platinum/iridium alloy, platinum, titanium or the like.

As an example, the linear stimulating lead 16 may have a diameter of between about 0.03 to 0.07 inches for spinal cord stimulation applications. An insertion cannula (not shown), e.g., a 14 gauge insertion needle may be used, while a 0.05 inch diameter stimulating lead is inserted within the cannula to help implant the stimulating lead 16. The stimulating lead 16 may come in a variety of lengths, e.g., 30, 50, 70 and 90 cm. A practitioner can extend the length of any of the available lead lengths by opting to use an extension lead 14 (shown in FIG. 1). The proximal male end of the extension lead 14 should be configured to be insertable into the lead connector of the IPG and the distal female end of the extension lead should be configured to accept the proximal connector end of the stimulating lead 16.

An embodiment of the percutaneous or linear stimulating lead 16 is isodiametric or substantially isodiametric, meaning that the diameter along the lead's entire length is constant or nearly constant. However, a linear lead 16 does not need to be entirely isodiametric. For example, the connector contacts 40 at the proximal end of a linear lead may be larger (oversized) or smaller in diameter compared to the remainder of the lead 16 or lead body 110 (shown in FIG. 5C). Likewise, the electrode contacts 17 may be larger (oversized) or smaller in diameter compared to the remainder of the lead 16 or lead body 110 (shown in FIG. 5C).

Figure 6A:
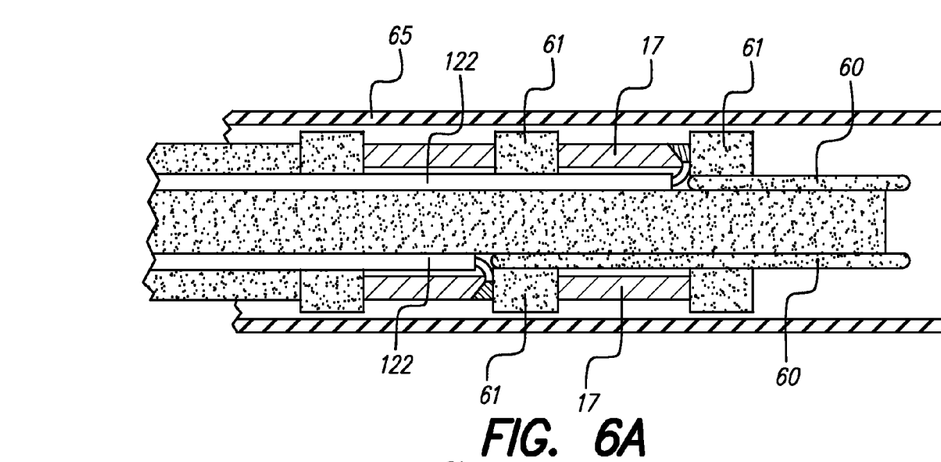
FIG. 6A shows a close-up, partial, longitudinal view of the lead assembly at the distal portion of the lead.

FIG. 6A shows a partial view of a longitudinal, cross-section at the distal end of an example linear lead. FIG. 6A shows a ring-like electrode contact 17 (which may be platinum, for example), multi-stranded conductor 122 and electrode contact spacer 61 (or an insulative material). The electrode spacer 61, which may be ring-like in configuration, may be made of polyurethane insulative material, e.g., Pellethane®. Monofilament 60, also may be made of thermoplastic Pellethane® material or other insulation material, e.g., polyester. During manufacture, the monofilament 60 may be inserted into the void spaces that are not filled by the conductor 50. A heat shrink tube 65 is also shown placed around the electrode contacts 17 and conductor 122 assembly. The heat shrink tube 65 may be PTFE (e.g., Teflon® material) or a polyester heat shrink material. The heat shrink tube is a tool that may be used during manufacturing to form the distal end of the percutaneous lead and is not part of the assembled stimulation lead.

Figure 6B:
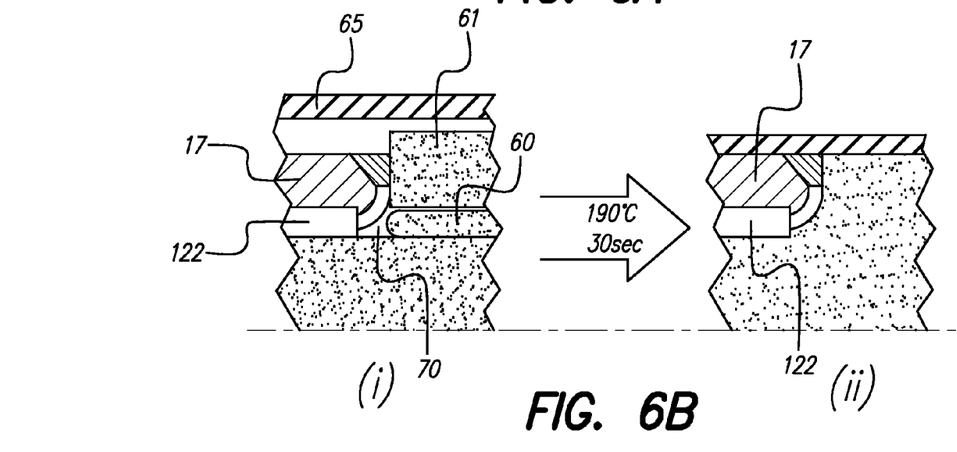
FIG. 6B depicts how polyurethane monofilament can be used to fill the voids and is incorporated as part of the distal end of the lead by applying heat.

FIG. 6B shows a two-frame, time-elapsed illustration of a partial view of the distal end of the linear lead as in FIG. 6A showing the conductor 122 connected (e.g., welded) to the electrode contact 17. The first frame (i) of FIG. 6B shows the sequence in which the monofilament 60 fills a large part of the void space 70 which space may be a conductor lumen or channel. The part of the lead assembly shown is then placed into a heat, for example, at 190 degrees Celsius for a period of 30 seconds. The heat that may be used, e.g., for a polyurethane material (e.g., Pellethane™ polyurethane), may range from about 140 to 250 degrees Celsius for a period of about between 15 to 120 seconds. However, importantly, the heat applied to the spacer and monofilament material, should be just below the melting temperature of the material. At this just-below-melting temperature, the electrode spacer 61 and monofilament 60 will reflow and thermally fuse together as shown in the second frame (ii). The spacer 61 and the monofilament 60 may be exactly the same material with the same melting temperature in order to facilitate thermal fusion. For example, the material may be the same implantable grade polyurethane such as Pellethane 55D or 75D. This illustrates one way the distal end of percutaneous lead can be manufactured.

The monofilament 60 may be of a different material than the electrode spacer 61 to alter the mechanical characteristic of the final lead assembly. The monofilament and spacer may have different melting points or very close melting points. The monofilament and spacers may be the same type of material but with different formulations, e.g., to provide different hardness. For example, the monofilament may be a 55D (durometer hardness) material and the spacer may be a 75D material. The predetermined temperature chosen to heat both the monofilament and spacers should cause at least one of the materials used to thermally reflow or, alternatively, to melt. In some cases, the temperature may be chosen that one material melts while the other material thermally reflows. FIGS. 6A and 6B show the distal end of the linear lead with monofilament filling a distal portion of the lead, including a part of the distal portion of the conductor lumens.

The terminal spacers 45 at the proximal end of the lead (shown in FIG. 3B) can be placed between adjacent terminal (connector) contacts 40. In one embodiment of the invention, the terminal spacers 45 may be oversized before assembly—that is, the terminal spacers, which may be made from polyurethane, PEEK, polysulfone, polyester, polyethylene or in some cases, silicone, may have an initial diameter that is larger than the final lead diameter. The terminal spacers may be ground, for instance by using centerless grinding, to a diameter that is the same as the terminal contacts.

Figure 7:
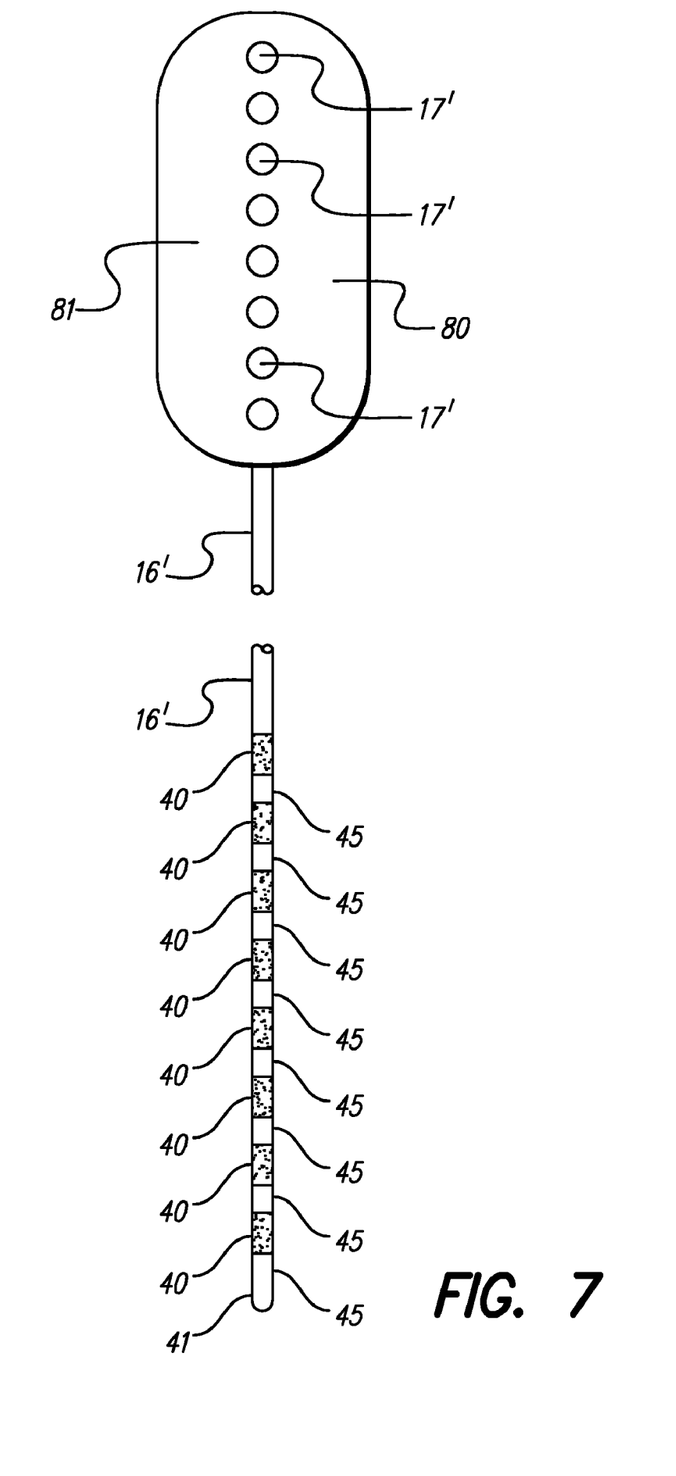
FIG. 7 shows an illustration of an exemplary paddle lead with a plurality of terminal contacts at the proximal end and plurality of contacts on the paddle surface.

FIG. 7 shows an example paddle lead 16' that includes a terminal or connector end having (a) terminal spacers 45 with epoxy applied within terminal spacers and terminal contacts 40, as well as between the terminal spacers and terminal contacts or (b) epoxy only between the terminal contacts 40.

The paddle lead 16' has a paddle portion 80 at the distal end of the lead. The paddle portion 80 has at least one flat surface 81 that has multiple electrode contacts 17' placed upon it. The paddle lead 16' shown has eight electrode contacts 17'. FIG. 7 also shows the terminal or proximal end of the lead. The terminal or proximal end of the lead has at least two terminal contacts 40. Adjacent terminal contacts 40 are separated by an electrically insulating material 45. This insulating material between the terminal contacts can be (1) terminal spacers that is an insulative material, e.g., epoxy, that is different from the lead body 110, which may be polyurethane or silicone; or (2) solely epoxy. The proximal connector end therefore can be used with many types of configurations at the distal end of the lead.

Figure 8:
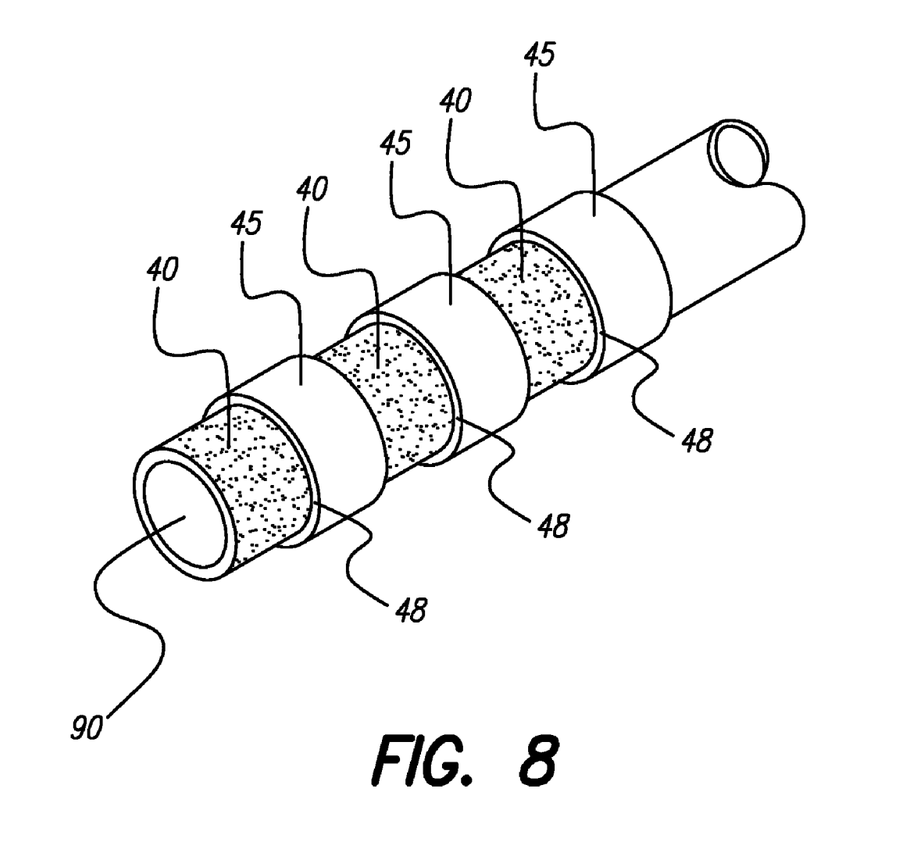
FIG. 8 shows a view of the terminal, connector end of a lead showing three terminal contacts.

FIG. 8 shows a close-up view of the proximal, connector end of a lead. This particular example only shows four terminal contacts 40 and three oversized terminal spacers 45 between adjacent terminal contacts. The oversized terminal spacers 45 can be ground down on the outside surface to match the diameter of the terminal contacts 40 in the final lead assembly. At the terminal end of the lead, the conductors 122, as shown in FIG. 4, are each individually welded to the terminal contacts 40. As can be seen from FIGS. 4 and 8, there is a space created inside the ring-shaped or ring-like terminal contacts because the conductors 122 do not occupy all the space within the terminal contacts and the ring-shaped or ring-like terminal spacers 45. Before proximal tip 41 is attached or glued onto the lead, FIG. 8 shows that there is an opening 90 at the most proximal terminal contact 40. This opening may be used during manufacturing to inject epoxy or other adhesive-like, insulating material into the space within or inside the ring-shaped terminal contacts or terminal spacers. The injected material, e.g., 85D epoxy (e.g., Hysol® epoxy), will fill the void inside the proximal end of the lead formed by terminal spacers and terminal contacts. In addition, some of the epoxy may fill any small void spaces 48 between adjacent terminal contacts and terminal spacers. If a lead body, having multiple lumens, such as shown in FIGS. 5A, 5B and 5C, is used, some of the injected epoxy can even migrate to the proximal portion of the lead body filling a portion of the lumens 116. The injection of the epoxy, can contribute to the ultimate stiffness and buckling strength of the proximal, connector end of the lead. In addition, the choice of the terminal spacer material can also contribute to ultimate stiffness and buckling strength of the proximal, connector end of the lead.

Figure 9:
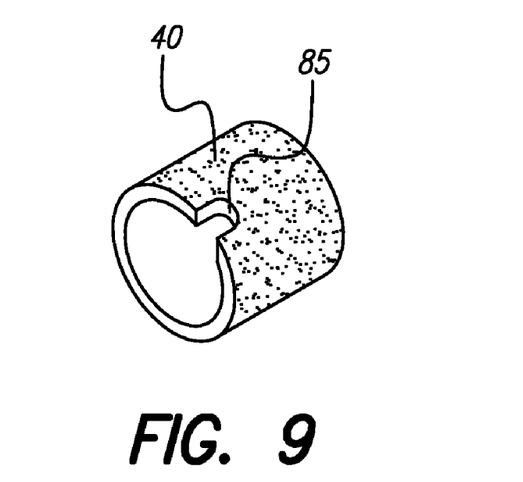
FIG. 9 shows a view of a ring shaped (or cylindrical ring-shaped) terminal contact having a slot at one end.

FIG. 9 shows one embodiment of the terminal contact 40 having a slot 85 cut out from the edge of the contact 40. This slot can be useful for welding the terminal contact to a conductor. The slot can be used to draw the end of the conductor into the slot while the conductor end is welded to the terminal contact. Similarly, the electrode contact at the distal end of a linear lead can also employ such a slot in a ring-like shaped electrode contact.

The following illustrates various embodiments of leads.

Example 1

Any Lead with a Proximal End Having Terminal Spacers and Epoxy

The lead has a plurality of connector (terminal) contacts, e.g., eight terminal contacts at the proximal end of the lead. Between the terminal contacts are spacers. The terminal contacts are shaped as rings or configured to be ring-like. In particular, the terminal contacts may be cylindrical rings. The terminal spacers are also formed into rings or configured to be ring-like. In particular they may also be cylindrical rings. The terminal spacers may be made from a number of materials. For example, the terminal spacers may be made from polyurethane, e.g., Pellethane™ 55D polyurethane. Other suitable materials include polyetherether ketone or polyarylether ketone (collectively, PEEK), polysulfone, polyester, silicone, and polyethylene. The choice of terminal spacer materials may be determined based on desired stiffness at the proximal end of the lead. For example PEEK and Polysulfone material may be harder than a 55D polyurethane. In addition, epoxy may be applied, e.g., injected, into void space within the terminal contact and terminal spacers and also applied in the small void spaces between a terminal contact and a terminal spacer. 85D Epoxy is also a harder and less flexible material than 55D.

Example 2

Linear Lead with Proximal, Terminal Spacers and Epoxy and Linear Distal End

The lead is linear and includes a proximal portion of the lead which is described in Example 1. Thus, the proximal end of the lead has a terminal spacer that is made from the group of materials: PEEK, polysulfone, polyester, silicone, and polyethylene. Epoxy may be applied, e.g., injected, in void spaces within the terminal spacers and terminal contacts and between a terminal spacer and an adjacent terminal contact. The distal end of the lead is linear and includes a plurality of electrode contacts, preferably formed into a ring or ring-like configuration, and more preferably a cylindrical ring. The distal end of the lead can optionally use electrode contact spacers, e.g., of polyurethane.

Example 3

Paddle Lead with Proximal End Terminal Spacers and Epoxy

The lead is not isodiametric, e.g., a paddle having at least one major flat surface and the proximal end of the lead includes terminal spacers between terminal contacts. The flat portion of the paddle includes a plurality of electrode contacts located on the flat portion of the paddle. The proximal or connector portion of the lead, however, is identical to the lead described in Example 1. Epoxy may be applied within the terminal spacers and terminal contacts and also in small voids spaces between a terminal spacer and a terminal contact.

Example 4

Any Lead with Epoxy Only Between the Terminal Contacts

The lead has a plurality of terminal contacts. The proximal end of the lead uses epoxy placed between the adjacent terminal contacts to form the connector.

Example 5

Linear Lead with Epoxy Only Between Terminal Contacts

As described in Example 4, the proximal end of the lead uses epoxy placed between adjacent terminal contacts to form the connector. The terminal contact are preferably rings or ring-like. No terminal spacer is used. The distal end of the lead is linear and includes a plurality of electrode contacts, preferably formed into a ring or ring-like configuration and, more preferably, a cylindrical ring.

Example 6

Paddle Lead with Epoxy Only Between Terminal Contacts

As described in Example 4, the proximal end of the lead uses epoxy between adjacent terminal contacts. The distal end of the lead has a paddle having at least one major flat surface. The flat surface of the paddle includes a plurality of electrode contacts.

Example 7

Lead Extension with Epoxy Only Between Terminal Contacts

A lead extension 14 (FIGS. 1 and 2) can have a proximal connector end with multiple, terminal contacts and epoxy only separating the terminal contacts as described in Example 4. The extension lead has a female connector or receptacle at the distal end of the extension lead. The female connector or receptacle may be configured to accommodate the proximal end of a stimulation lead, e.g., a linear or paddle lead as described in Examples 1-6 having an identical proximal connector configuration as the extension lead itself. Or, alternatively, the female connector or receptable may be configured to accept the proximal end of a stimulation lead, which proximal end of the stimulation lead is not compatible with the connector block 5 of IPG 12. For example, different manufacturers use different connectors at the ends of their stimulation leads and are therefore not compatible with IPG connector blocks of another manufacturer. The extension lead can be made to connect the IPG to the stimulation lead and hence "adapt" the stimulation lead to the IPG. Such an extension lead is actually referred to as a "lead adapter" because it adapts a stimulation lead to a normally incompatible IPG.

Example 8

Lead Extension with Terminal Spacers

A lead extension 14 (FIGS. 1 and 2) can have a connector with a multiple terminal contacts at the proximal end. As described in Example 1, the terminal contacts 45 may be separated by terminal spacers 40 made from the following body implantable materials as previously discussed: PEEK, polysulfone, polyester, silicone, and polyethylene. A second insulative, adhesive-like material, e.g., epoxy may be used to fill voids within the terminal contacts and terminals spacers not filled by conductor wire, and also voids within the terminal contact and terminal spacer and voids between an adjacent terminal contact and a terminal spacer. The female end of the extension lead can be used to accommodate a stimulation lead, e.g., a linear or paddle lead having an identical proximal connector configuration as the extension lead or, alternatively, a stimulation lead that has a connector configuration that cannot directly fit into and hence incompatible with the connector block 5 of the IPG 12. Such an extension lead is actually referred to as a "lead adapter" because it adapts a stimulation lead to a normally incompatible IPG.

Methods of Making Stimulation Leads, Extension Leads or Lead Adapters

The following steps illustrates specific steps for making a proximal connector end of a stimulation lead, an extension lead or a lead adapter and additional steps for making a stimulation lead, an extension lead or a lead adapter. Embodiments of the method can include one or more of the following steps (although not necessarily in the order presented).

An embodiment of the method of manufacturing a lead with a terminal, proximal end and a distal end and an insulative covering is disclosed. The method includes: placing a plurality of conductive terminal contacts at the terminal, proximal end of the stimulation lead; placing at least one electrode contact on the distal end of the lead; connecting at least one conductor wire to one of the conductive terminal contacts; placing a terminal spacer between a pair of adjacent conductive terminal contacts; and applying epoxy in any voids within the at least one spacer and terminal contact and between at least one spacer and terminal contact.

In an alternative method of manufacturing a lead, the stimulation lead has a terminal end and a distal end and an insulative covering. The method includes: providing a lead having a plurality of conductor lumens; placing a plurality of conductive terminal contacts at the distal end of the stimulation lead; connecting at least one conductor wire to one of the conductive terminal contacts; and placing epoxy between two terminal contacts.

As further steps to the method of manufacturing a lead, specific types of leads may be manufactured. For example, a paddle stimulation lead may be made by connecting a paddle with electrode contacts at the distal part of the lead. Alternatively, a linear lead may be produced by connecting a linear distal portion to the lead. Still yet, an extension lead may be produced by connecting a female receptacle connector end at the distal end of the lead, the female connector configured to accept the proximal end of a stimulation lead. Still further, an extension that is a lead adapter may be produced by connecting a female connector end to the lead, the female connector end having a configuration that is compatible and accepts the proximal end of a lead which is not compatible with the IPG connector.

A more detailed embodiment of making a lead having terminal spacers and epoxy in the void spaces within the spacers and terminal contacts and voids between spacers and terminal contacts is as follows: a braided or bundled, insulated, multi-filament conductor, e.g., having between 2 and 200 filaments, can be ablated of insulation at one end to expose the conductor; the exposed end of the conductor can be welded to a terminal (proximal) contact (located on the distal end lead assembly); terminal spacers (which may be made of polyurethane, PEEK, Polysulfone, polyester, polyethylene or silicone) may be placed between the terminal contacts; if a lead body with a multiple conductor lumens is used, each end of the conductor cable can be inserted through the corresponding conductor lumens in the lead body; the terminal spacers can be placed between each ring-like terminal contact at the distal end of the lead assembly; the spacers 61 may be "oversized", meaning that they may have a diameter greater than the lead body 110 and in addition, the diameter of the terminal contacts 17 may be oversized compared to the diameter of the lead body 110; the distal end of each conductor cable can be welded to the ring or ring-shaped (ring-like) terminal contact; and epoxy may injected into the middle opening of the most proximal terminal spacer (or in some cases the most proximal terminal contact). This epoxy will fill the void space with the terminal spacers and terminal contacts and some of the epoxy may be forced through the void spaces between a terminal spacer and terminal contact and thereby fill those void spaces. The steps described above can be performed in a different sequence and some steps may be optionally left out.

A detailed embodiment of making a lead having only epoxy between terminal contacts may be as follows: a braided or bundled, insulated, multi-filament conductor, e.g., having between 2 and 200 filaments, can be ablated of insulation at one end to expose the conductor; the exposed end of the conductor can be welded to a terminal (proximal) contact (located on the distal end lead assembly); if a lead body with a multiple conductor lumens is used, each end of the conductor cable can be inserted through the corresponding conductor lumens in the lead body; the distal end of each conductor cable can be welded to the ring-shaped or ring-like terminal contact; the terminal contacts may be held in a mold which keeps a prescribed space between the next terminal contact; and epoxy may applied, e.g., injected into the open areas between the terminal contacts to fill those spaces. The epoxy is, in a sense, casted over the proximal end and conductor wires. After the epoxy has cured, the proximal lead end may be ground, e.g., with centerless grinding, to a prescribed diameter at this point or later in the manufacturing method. The steps described above can be performed in a different sequence and some steps may be optionally left out.

The proximal, connector end of the lead may be assembled first and then the distal end may also be assembled. (It is also possible that the order can be reversed and the distal end is assembled first.) A specific example of a method of making the distal end of a linear (percutaneous) lead was described in detail in the U.S. patent application Ser. No. 11/329,907, the parent application to the present application. This method includes using a polyurethane monofilament placed inside void spaced as shown in FIG. 6A and inside any empty conductor lumens 116 at the distal end of the lead; a heat shrink tube or wrap, preferably, made from PTFE (Teflon) or polyester, can be placed over the distal end of the lead assembly and over the electrode array; this distal end can be placed into a high temperature block, e.g., between about 140-250 degrees Celsius for a period of about 30 to 120 seconds; the distal assembly can be removed from the heat and the shrink tube or wrap can be removed; and optionally, the distal tip of the lead can be formed using an RF welder.

Post processing of the linear lead may not be required if the diameter of the terminal spacers, the terminal contacts, the electrode spacers and the electrode contacts are the same as the lead body. However, if any of these parts are oversized, a centerless grinding process may be used, if desired, to remove excess outer material of the intermediate lead assembly that has the proximal end and distal end assembled.

It is also possible to produce other types of leads. For example, once the proximal end of the lead is made, either with terminal spacers and epoxy or solely with epoxy between the terminal contacts, the method of manufacturing the lead can proceed to making a particular configuration of the distal part of the lead, i.e., (a) making a paddle with multiple contacts or (b) making a female connector of an extension lead or lead adapter. As will be understood by those skilled in the art, known methods of making these particular distal parts of leads and lead extensions may be used.

The above methods describe how a lead may be made having a proximal end made with epoxy between the terminal contacts or, alternatively, a lead having a proximal end with terminal spacers and a second material such as epoxy. The terminal spacers can be made from various materials: polyurethane, PEEK, polysulfone, polyethylene, polyester or silicone.

In summary, in some embodiments the lead will be a linear or percutaneous lead. Such a lead can have an epoxy terminal at the proximal portion of the lead. In other embodiments, the percutaneous lead will employ spacers between the terminal contacts.

In other embodiments the lead is not be linear, i.e., it may be a paddle type lead, which is not isodiametric. The lead will also have a plurality of terminal contacts and a plurality of electrode contacts at the paddle, distal end of the lead. The proximal, terminal end of the lead can either have material between the terminal contacts or, alternatively, the proximal end can employ terminal spacers. Such spacers can be the various materials listed: polyurethane, PEEK, polysulfone, polyethylene, polyester or silicone.

In yet other embodiments, the lead is an extension lead that may have a proximal end that uses terminal spacers and epoxy at the terminal end or solely epoxy between two terminal contacts. More particularly, the extension lead may be an adapter lead.

Although the lead and method of making the lead are described in the context of a spinal cord stimulation, e.g., percutaneous or linear leads, paddle leads, or extension leads, it will be understood by those skilled in the art that the same lead, albeit with appropriate dimensions for a particular application, may be used for other treatment applications such as deep brain stimulation and peripheral nerve stimulation.

While the invention herein disclosed has been described by means of specific embodiments and applications thereof, numerous modifications and variations could be made thereto by those skilled in the art without departing from the scope of the invention set forth in the claims.

What is claimed is:

1. A method of making a stimulation lead having a proximal end and a distal end, the method comprising:
   placing a plurality of conductive terminal contacts at the proximal end of the stimulation lead;
   placing a plurality of electrode contacts at the distal end of the stimulation lead;
   connecting a plurality of conductor wires to the plurality of terminal contacts such that for each of the plurality of terminal contacts a different conductor wire of the plurality of conductor wires connects to the terminal contact, wherein the plurality of conductor wires comprises a first conductor wire and a second conductor wire, wherein the first conductor wire extends within a first conductor lumen of a plurality of conductor lumens defined in a lead body of the stimulation lead, wherein the second conductor wire extends within a second conductor lumen of the plurality of conductor lumens defined in the lead body of the stimulation lead, wherein the lead body defines a stylet lumen configured and arranged for receiving a stylet, and wherein the plurality of conductor lumens and the stylet lumen each extend along a substantial length of the stimulation lead from the proximal end;

placing a terminal spacer between a pair of adjacent conductive terminal contacts of the plurality of conductive terminal contacts;

and applying epoxy to the proximal end of the stimulation lead such that the epoxy at least partially fills the conductor lumens in proximity to the proximal end of the stimulation lead.

2. The method of claim 1, wherein the terminal spacer is made from material selected from the group consisting of polyetherether ketone, polyarylether ketone (collectively, PEEK) and polysulfone.

3. The method of claim 1, wherein the terminal spacer is made from polyurethane.

4. The method of claim 1, wherein the distal end of the lead is configured as a paddle and wherein the lead is a paddle lead.

5. The method of claim 1, wherein the distal end of the lead is configured as linear and wherein the lead is a percutaneous, linear lead.

6. The method of claim 1, wherein the epoxy has a durometer of at least 85D, and wherein the lead body has a durometer that is no more than 55D.

7. The method of claim 1, wherein the stimulation stylet lumen is defined in the lead body such that the plurality of conductor lumens surrounds the stylet lumen.

8. The method of claim 1, wherein the plurality of terminal contacts are in the form of rings having at least one slot on the edge of the ring.

9. The method of claim 1, wherein the terminal spacer is made from material selected from the group consisting of silicone, polyethylene and polyester.

10. The method of claim 1, further comprising attaching a proximal tip to the proximal end of the stimulation lead after applying the epoxy to the proximal end of the stimulation lead.

11. A stimulation lead having a proximal end, a distal end and an insulative covering, the lead comprising:
a plurality of electrode contacts on the distal end of the stimulation lead;
a plurality of conductive terminal contacts at the proximal end of the stimulation lead;
a lead body extending along a substantial length of the stimulation lead, the lead body defining a plurality of conductor lumens and a stylet lumen, wherein the plurality of conductor lumens and the stylet lumen extend along a length of the lead body, wherein the plurality of conductor lumens comprises a first conductor lumen and a second conductor lumen;
a plurality of conductor wires, each conductor wire of the plurality of conductor wires connecting a different one of the plurality of conductive terminal contacts to one of the electrode contacts, wherein the plurality of conductor wires comprises a first conductor wire and a second conductor wire, wherein the first conductor wire extends along the first conductor lumen and the second conductor wire extends along the second conductor lumen;
a terminal spacer that is positioned between a first and a second adjacent terminal contacts of the plurality of conductive terminal contacts; and
epoxy that is within at least some portion of the plurality of conductor lumens in proximity to the proximal end of the stimulation lead.

12. The lead of claim 11, wherein the terminal spacer is made from a material selected from the group consisting of PEEK and polysulfone.

13. The lead of claim 11, wherein the epoxy has a durometer of at least 85D, and wherein the lead body has a durometer that is no more than 55D.

14. The lead of claim 11, wherein the terminal spacer is made from the material selected from the group consisting of polyester, polyethylene, and silicone.

15. The lead of claim 11, wherein the lead body is a one-piece component made from thermoplastic polyurethane.

16. The lead of claim 11, wherein the stylet lumen is defined in the lead body such that the plurality of conductor lumens surrounds the stylet lumen.

17. The lead of claim 11, wherein the plurality of terminal contacts are in the form of cylindrical rings having at least one slot on the edge of the cylindrical ring.

18. The lead of claim 11, wherein the distal tip of the lead includes a radiopaque marker.

19. The lead of claim 11, wherein at least one of the plurality of conductor wires is a multi-filar conductor wire.

20. The lead of claim 11, wherein the distal end of the lead is linear and the lead is percutaneous.

21. The lead of claim 11, wherein distal end of the lead is configured as a paddle and wherein the lead is a paddle lead.

22. The lead of claim 11, further comprising: a retention sleeve disposed on the proximal end of the stimulation lead, the retention sleeve configured to contact a set screw.

23. The lead of claim 11, wherein the plurality of electrode contacts are configured as rings.

24. The stimulation lead of claim 11, further comprising a proximal tip covering an injection aperture defined at the proximal end of the lead.

25. The stimulation lead of claim 11, wherein each conductor wire of the plurality of conductor wires extends within a different conductor lumen of the plurality of conductor lumens.

26. A stimulation lead having a proximal end and a distal end and an insulative covering, the lead comprising:
a plurality of electrode contacts on the distal end of the stimulation lead;
a plurality of conductive terminal contacts disposed at the proximal end of the stimulation lead, the plurality of conductive terminal contacts comprising a first conductive terminal contact and a second conductive terminal contact;
a lead body extending along a substantial length of the stimulation lead, the lead body defining a plurality of conductor lumens and a stylet lumen, wherein the plurality of conductor lumens and the stylet lumen extend along a length of the lead body, wherein the plurality of conductor lumens comprises a first conductor lumen and a second conductor lumen;
a plurality of conductor wires, each conductor wire of the plurality of conductor wires connecting a different one of the plurality of conductive terminal contacts to one of the plurality of electrode contacts, wherein the plurality of conductor wires comprises a first conductor wire and a second conductor wire, wherein the first conductor wire extends along the first conductor lumen and the second conductor wire extends along the second conductor lumen;

a terminal spacer that is positioned between the first and the second terminal contacts, wherein the terminal spacer is selected from the group consisting of PEEK and polysulfone; and epoxy disposed within at least some portion of the plurality of conductor lumens in proximity to the proximal end of the stimulation lead.

27. The stimulation lead of claim 26, wherein epoxy is placed between the terminal spacer and either the first terminal contact or the second terminal contact, and wherein epoxy is placed within voids in the stimulation lead inside the terminal spacer and inside at least one of the terminal contacts.

28. The stimulation lead of claim 26, wherein the plurality of conductor lumens and the stylet lumen are defined in a one-piece component.

* * * * *